US012623983B2

(12) United States Patent
Fukuda et al.

(10) Patent No.: US 12,623,983 B2
(45) Date of Patent: May 12, 2026

(54) GAS SEPARATION SYSTEM AND METHOD FOR PRODUCING METHANE-ENRICHED GAS

(71) Applicant: UBE Corporation, Ube (JP)

(72) Inventors: Nobuhiko Fukuda, Ube (JP); Hiroki Inde, Ube (JP); Takumi Fukunaga, Ube (JP); Tomohide Nakamura, Ube (JP)

(73) Assignee: UBE Corporation, Ube (JP)

( * ) Notice: Subject to any disclaimer, the term of this patent is extended or adjusted under 35 U.S.C. 154(b) by 0 days.

(21) Appl. No.: 18/871,317

(22) PCT Filed: Jul. 12, 2023

(86) PCT No.: PCT/JP2023/025794
§ 371 (c)(1),
(2) Date: Mar. 27, 2025

(87) PCT Pub. No.: WO2024/014493
PCT Pub. Date: Jan. 18, 2024

(65) Prior Publication Data
US 2025/0223246 A1 Jul. 10, 2025

(30) Foreign Application Priority Data
Jul. 14, 2022 (JP) ................................. 2022-113548

(51) Int. Cl.
*C07C 7/144* (2006.01)
*C07C 7/00* (2006.01)
*C07C 9/04* (2006.01)

(52) U.S. Cl.
CPC .............. *C07C 7/144* (2013.01); *C07C 7/005* (2013.01); *C07C 9/04* (2013.01)

(58) Field of Classification Search
None
See application file for complete search history.

(56) References Cited

U.S. PATENT DOCUMENTS

| | | | |
|---|---|---|---|
| 6,197,090 B1 | 3/2001 | Yamashita et al. | |
| 6,428,606 B1 * | 8/2002 | Gottschlich .......... | B01D 53/225 95/50 |

(Continued)

FOREIGN PATENT DOCUMENTS

| | | |
|---|---|---|
| JP | 52-114475 A | 9/1977 |
| JP | 2000-33222 A | 2/2000 |

(Continued)

*Primary Examiner* — Tam M Nguyen
(74) *Attorney, Agent, or Firm* — Knobbe, Martens, Olson & Bear, LLP

(57) ABSTRACT

A gas separation system for enriching methane contained in raw material mixed gas including at least carbon dioxide and methane by supplying the raw material mixed gas to a gas separation membrane unit in which the gas separation system includes a first gas separation membrane unit and a second gas separation membrane unit. A raw material mixed gas supply line is connected to a gas inlet of the first gas separation membrane unit. The non-permeated gas outlet of the first gas separation membrane unit and the gas inlet of the second gas separation membrane unit are connected by a first non-permeated gas discharge line. A second non-permeated gas recovery line is connected to the second non-permeated gas outlet of the second gas separation membrane unit. The first permeated gas outlet of the first gas separation membrane unit and the second permeated gas outlet of the second gas separation membrane unit are connected to the raw material mixed gas supply line by a first permeated gas recycle line and a second permeated gas recycle line, respectively. The line includes a permeated gas discharge line for at least partially discharging the permeated gas of the first gas separation membrane unit to the outside of the system.

13 Claims, 1 Drawing Sheet

(56)     References Cited

U.S. PATENT DOCUMENTS

| | | | | |
|---|---|---|---|---|
| 10,610,834 | B2 * | 4/2020 | Kawai | B01D 69/02 |
| 11,083,991 | B2 * | 8/2021 | Barraud | C07C 7/144 |
| 11,491,440 | B2 * | 11/2022 | Terrien | C07C 7/144 |
| 11,731,076 | B1 * | 8/2023 | O'Brien | C07C 7/005 |
| | | | | 585/818 |
| 12,337,276 | B2 * | 6/2025 | Pedersen | C10L 3/104 |
| 2004/0099138 | A1 * | 5/2004 | Karode | C07C 7/11 |
| | | | | 95/231 |
| 2015/0336046 | A1 | 11/2015 | Ungerank et al. | |
| 2016/0229771 | A1 * | 8/2016 | Paget | B01D 53/226 |
| 2019/0030482 | A1 * | 1/2019 | Ding | B01D 71/5211 |
| 2019/0224617 | A1 * | 7/2019 | Mitariten | B01D 71/76 |
| 2020/0254383 | A1 * | 8/2020 | Roodbeen | B01D 53/227 |
| 2020/0316516 | A1 | 10/2020 | Wu et al. | |

FOREIGN PATENT DOCUMENTS

| | | | |
|---|---|---|---|
| JP | 2013-128868 | A | 7/2013 |
| JP | 2016-505354 | A | 2/2016 |
| JP | 2019-520198 | A | 7/2019 |
| JP | 2020-163282 | A | 10/2020 |
| JP | 2022-113214 | A | 8/2022 |

* cited by examiner

GAS SEPARATION SYSTEM AND METHOD FOR PRODUCING METHANE-ENRICHED GAS

CROSS-REFERENCE TO RELATED APPLICATIONS

This application is the U.S. National Phase under 35 U.S.C. § 371 of International Application PCT/JP2023/025794, filed Jul. 12, 2023, designating the U.S., and published in Japanese as WO 2024/014493 on Jan. 18, 2024 which claims priority to Japanese Patent Application No. 2022-113548 filed Jul. 14, 2022, the entire content of which is incorporated herein by reference.

TECHNICAL FIELD

The present invention relates to a gas separation system for separating a mixed gas using a plurality of gas separation membrane units, and a method for producing a methane-enriched gas using the same.

BACKGROUND ART

As a method of separating a mixed gas containing two or more kinds of different gases into respective gases, a membrane separation method using a difference in permeation rate of a gas with respect to a membrane is known. In this method, a high-purity high-permeability gas and/or a high-purity low-permeability gas, which are target gases, can be obtained by collecting the permeated gas and/or the non-permeated gas. The permeation rate, which is the permeation volume per unit membrane area, unit time, and unit partial pressure difference of each gas contained in the mixed gas with respect to the membrane, can be expressed by P' (unit: $\times 10^{-5}$ cm$^3$ (STP)/cm$^2$·sec. cmHg). The gas separation selectivity of the membrane can be expressed as a ratio of (permeation rate of high permeability gas/permeation rate of low permeability gas).

In general, in a gas separation membrane, a membrane having a high gas separation selectivity has a low gas permeation rate, whereas a membrane having a high gas permeation rate has a low gas separation selectivity. Therefore, in the case where the low-permeability gas is recovered from the mixed gas using the single-stage gas separation membrane, when the purity of the recovered gas is constant, the recovery rate becomes high when the membrane having high gas separation selectivity is used. However, due to the low permeation rate, it is necessary to increase the membrane area or to increase the operating pressure. On the other hand, in the case of a membrane having a high permeation rate, it is not necessary to increase the membrane area or the operating pressure, but the recovery rate is low because of the low gas separation selectivity.

In general, a gas separation membrane having selective gas permeability is used as a gas separation membrane module in which the gas separation membrane is accommodated in a container provided with at least a gas inlet, a permeated gas outlet, and a non-permeated gas outlet. The gas separation membrane is mounted in the container such that a space on the gas supply side and a space on the gas permeation side are isolated from each other. In a gas separation system, a gas separation membrane unit in which a plurality of gas separation membrane modules are combined in parallel is generally used in order to obtain a required membrane area. Since the plurality of gas separation membrane modules constituting the gas separation membrane unit share a gas inlet, a non-permeated gas outlet, and a permeated gas outlet, the gas separation membrane unit acts as a substantially large gas separation membrane module.

In order to recover a target low-permeability gas at a high purity and a high recovery rate, a method of using a system provided with this gas separation membrane unit in multiple stages is known. Examples of the multistage gas separation system include a system that further separates the first-stage non-permeated gas enriched with the low-permeability gas in order to improve purity, and a system that recovers the low-permeability gas contained in the first-stage permeated gas in order to improve recovery rate.

PTL 1 is configured to: pressurize, by a compressor, a mixed gas containing an easily permeable gas that easily permeates a gas separation membrane and a hardly permeable gas that hardly permeates the gas separation membrane to supply the mixed gas to a first membrane separation unit provided with a first gas separation membrane; taking out a first permeated gas that permeated the first gas separation membrane; and supply a first residual gas that does not permeate the gas separation membrane and is discharged from the first membrane separation unit to a second membrane separation unit provided with a second gas separation membrane, a gas purification method of circulating and supplying a second permeated gas permeated through the second gas separation membrane to the raw material gas to perform gas purification, wherein a part of the first permeated gas obtained by passing through the first gas separation membrane is circulated and supplied to the raw material gas side, the mixed gas and the circulated and supplied first permeated gas are purified by the first gas separation membrane, and the remainder of the obtained first permeated gas is recovered in performing gas purification. In the PTL 1, since the purity of hydrogen in the product gas decreases when the flow rate of the raw material gas decreases at the time of separating the easily permeable gas such as hydrogen, in order to prevent this, a part of the permeated gas that permeated the first gas separation membrane is circulated to the raw material gas side instead of taking out all the permeated gas of the first gas separation membrane at the time of decreasing the flow rate of the raw material gas.

PTL 2 describes a two-stage gas separation membrane system for recovering methane, a low permeability gas, from a mixed gas comprising methane and carbon dioxide."

CITATION LIST

Patent Literature

PTL. 1 U.S. Pat. No. 6,197,090B1
PTL. 2 Japanese Patent Laid-Open No. 2013-128868

SUMMARY OF INVENTION

Conventionally, it has been known that methane is recovered from a mixed gas containing carbon dioxide and methane by a two-stage gas separation membrane, but in a conventional system such as that described in PTL 2, there is room for improvement in compatibility between the recovery rate and purity of methane.

In addition, the invention described in PTL 1 aims at separation of easily permeable gas, relates to a decrease in purity of high-permeability gas when the flow rate of the raw material gas is decreased, and does not consider achieving both purity and recovery rate of low-permeability gas.

An object of the present invention is to improve the purity and recovery rate of methane to be recovered in a gas separation system in which methane is recovered from a raw material mixed gas containing carbon dioxide and methane using a gas separation membrane.

The present invention provides the following [1] to [8].

[1]
A gas separation system for enriching methane contained in raw material mixed gas comprising at least carbon dioxide and methane by supplying the raw material mixed gas to a gas separation membrane unit, wherein the gas separation system comprise a first gas separation membrane unit and a second gas separation membrane unit, each of the gas separation membrane units comprise at least a gas inlet, a permeated gas outlet, and a non-permeated gas outlet, the non-permeated gas outlet of the first gas separation membrane unit and the gas inlet of the second gas separation membrane unit are connected by a non-permeated gas discharge line, the raw material mixed gas supply line is connected to the gas inlet of the first gas separation membrane unit, a compression part is interposed in the raw material mixed gas supply line, and a first permeated gas recycle line connects the permeated gas outlet of a first gas separation membrane unit and the a position on a suction side of the compression part on the raw material mixed gas supply line, the first permeated gas recycle line comprises a permeated gas discharge line for at least partially discharging the permeated gas discharged from the first gas separation membrane unit to the outside of the gas separation system, the permeated gas outlet of the second gas separation membrane unit and a position on the suction side of the compression part in the raw material mixed gas supply line are connected by a second permeated gas recycle line, and enriched methane is recovered from the non-permeated gas outlet of the second gas separation membrane unit.

[2]
The gas separation system according to [1], wherein the operating temperature of the first gas separation membrane unit is different from the operating temperature of the second gas separation membrane unit.

[3]
The gas separation system according to [2], wherein the operating temperature of the second gas separation membrane unit is higher than the operating temperature of the first gas separation membrane unit.

[4]
The gas separation system according to [3], wherein a heating unit is disposed in the middle of a non-permeated gas discharge line connecting the non-permeated gas outlet of the first gas separation membrane unit and the gas inlet of the second gas separation membrane unit.

[5]
The gas separation system according to [1], wherein the gas separation selectivity of the first gas separation membrane unit is different from the gas separation selectivity of the second gas separation membrane unit.

[6]
The gas separation system according to [5], wherein the gas separation selectivity of the second gas separation membrane unit is lower than the gas separation selectivity of the first gas separation membrane unit.

[7]
The gas separation system according to any one of [1] to [7], wherein a ratio of the recycle flow rate $F_4$ circulated to the first gas separation membrane unit by the first permeated gas recycle line to the permeated gas flow rate $F_1$ of the first gas separation membrane unit is 0.5% or more and 60% or less.

[8]
A method for producing methane-enriched gas enriched in methane by supplying raw material mixed gas comprising at least carbon dioxide and methane to gas separation system, wherein the gas separation system comprises a first gas separation membrane unit and a second gas separation membrane unit, each of the gas separation membrane units comprises at least a gas inlet, a permeated gas outlet, and a non-permeated gas outlet, the non-permeated gas outlet of the first gas separation membrane unit and the gas inlet of the second gas separation membrane unit are connected by a non-permeated gas discharge line, the raw material mixed gas supply line is connected to the gas inlet of the first gas separation membrane unit, a compression part is interposed in the raw material mixed gas supply line, and a first permeated gas recycle line connects a permeated gas outlet of a first gas separation membrane unit and the a position on a suction side of the compression part on the raw material mixed gas supply line, the first permeated gas recycle line comprises a permeated gas discharge line for at least partially discharging the permeated gas discharged from the first gas separation membrane unit to the outside of the gas separation system, and the permeated gas outlet of a second gas separation membrane unit and a position on the suction side of the compression part in the raw material mixed gas supply line are connected by a second permeated gas recycle line; and the method comprises recovering enriched methane from the non-permeated gas outlet of the second gas separation membrane unit.

DESCRIPTION OF EMBODIMENTS

Figure 1:
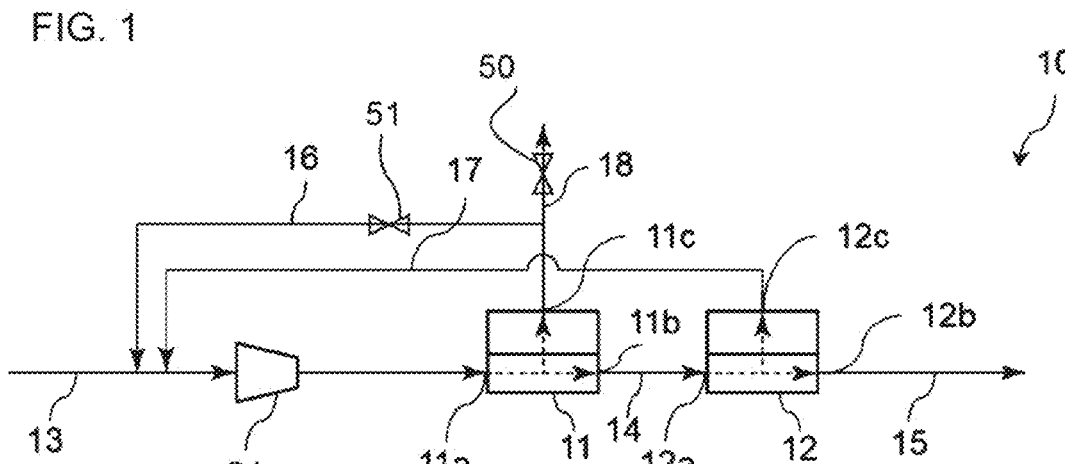
FIG. 1 is a schematic diagram showing a configuration of a gas separation system according to a first embodiment of the present invention.

Hereinafter, the present invention will be described based on preferred embodiments thereof with reference to the drawings.

First, a gas separation system 10 according to a first embodiment of the present invention will be described with reference to FIG. 1. A gas separation system 10 shown in FIG. 1 includes a first gas separation membrane unit 11 and a second gas separation membrane unit 12. As each of the gas separation membrane units 11 and 12, for example, as shown in FIG. 2, a module 40 in which a gas separation membrane 30 made of a hollow fiber membrane or the like and having gas selective permeability is accommodated in a casing 31 can be used. The gas separation membrane units 11 and 12 of the present embodiment shown in FIG. 1 use, for example, one gas separation membrane module 40 shown in FIG. 2, or include a plurality of such modules 40 arranged in parallel. Two opposing surfaces of the casing 31 of the module 40 are opened to form an opening 32. It should be noted that the opening 32 is for inserting the gas separation membrane 30 into the casing 31, and is not an opening of the gas separation membrane 30. The gas separation membrane 30 is accommodated in the casing 31 through the opening 32. In the case where the gas separation membrane 30 is formed of a hollow fiber membrane bundle, the gas separation membrane 30 is housed in the casing 31 in the housed state so that each end portion of the hollow fiber membrane is opened in the vicinity of each opening 32 of the casing 31."

In a state where the gas separation membrane 30 is housed in the casing 31, the gas separation membrane 30 is fixed to the inner wall of the casing 31 by the tube plates 33 and 34 at positions of both end portions in the Y direction which is the extending direction of the hollow fiber membrane. Each opening 32 of the casing 31 is closed by lids 35 and 36. The lid 35 is provided with a gas inlet 37. On the other hand, the lid 36 is provided with a non-permeated gas outlet 38. The mixed gas to be separated is introduced into the module from the gas inlet 37 of the lid 35. Of the introduced gas, the gas that has permeated the gas separation membrane 30 is discharged to the outside of the module through a permeated gas outlet 39 provided in the casing 31. On the other hand, the non-permeated gas that has not permeated the gas separation membrane 30 is discharged from the non-permeated gas outlet 38 of the lid 36 to the outside of the module. In some cases, a purge gas supply port (not shown) may be provided in the casing 31. Although the separation membrane module of FIG. 2 has been described as an example, the present invention can be applied to separation membrane modules having other configurations, and can be applied to, for example, a shell feed type module.

Returning to FIG. 1, the first gas separation membrane unit 11 and the second gas separation membrane unit 12 are connected in series. Specifically, the first gas separation membrane unit 11 and the second gas separation membrane unit 12 are linked by connecting the non-permeated gas outlet 11b of the first gas separation membrane unit 11 and the gas inlet 12a of the second gas separation membrane unit 12 by the first non-permeated gas discharge line 14.

A raw material mixed gas supply line 13 for supplying a raw material mixed gas from a mixed gas source (not shown) as a raw material to the first gas separation membrane unit 11 is connected to the gas inlet 11a of the first gas separation membrane unit 11. A compression part 21 is disposed in the middle of the raw material mixed gas supply line 13. The compression part 21 is installed for the purpose of pressurizing the mixed gas supplied from the mixed gas source. Further, it is installed for the purpose of pressurizing the permeated gas when the first permeated gas discharged from the first gas separation membrane unit 11 is returned to the first gas separation membrane unit 11, and pressurizing the permeated gas when the second permeated gas discharged from the second gas separation membrane unit 12 is returned to the first gas separation membrane unit 11.

In the first gas separation membrane unit 11, the permeated gas outlet 11c is connected to the position on the suction side of the compression part 21 in the raw material mixed gas supply line 13 by the first permeated gas recycle line 16. In the second gas separation membrane unit 12, the permeated gas outlet 12c is connected to the position of the suction side of the compression part 21 in the raw material mixed gas supply line 13 by the second permeated gas recycle line 17.

A second non-permeated gas recovery line 15 for taking out the concentrated and enriched non-permeated gas is connected to the non-permeated gas outlet 12b of the second gas separation membrane unit 12.

Figure 2:
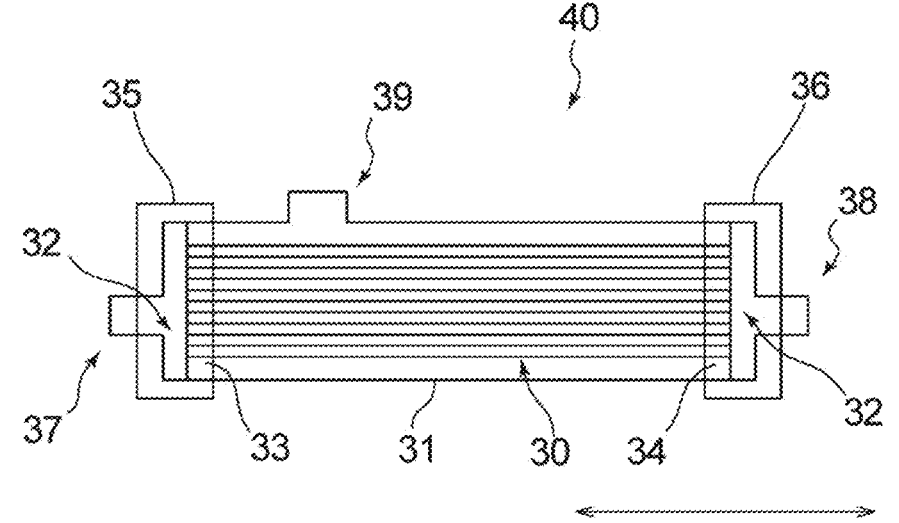
FIG. 2 is a schematic view showing a structure of an example of a gas separation membrane module used in the gas separation system of the present invention.

As shown in FIG. 1, the first permeated gas recycle line 16 is provided with a first permeated gas discharge line 18 for discharging a part of the permeated gas discharged from the first gas separation membrane unit 11 to the outside of the system. The discharge to the outside of the system means, for example, that the gas is taken out of the flow path of the gas composed of the first gas separation membrane unit 11 and the second gas separation membrane unit 12. The first permeated gas discharge line 18 is connected to the outside of the system on its discharge side (outlet side) without being connected to either the first gas separation membrane unit 11 or the second gas separation membrane unit 12. In FIG. 1, the first permeated gas discharge line 18 is provided as a branch line from the first permeated gas recycle line 16. The branch line branches out of the system from a position in the middle of a connection point between the gas outlet 11c and the raw material mixed gas supply line 13 in the first permeated gas recycle line 16. The ratio of the permeated gas (Hereinafter, it is also referred to as "discharge permeated gas".) discharged to the outside of the system through the first permeated gas discharge line 18 to the total permeated gas discharged from the first gas separation membrane unit 11 can be adjusted by a flow control valve 50 provided in the middle of the first permeated gas discharge line 18 and/or a flow control valve 51 provided in the first permeated gas recycle line 16.

The operation of the gas separation system 10 of the present embodiment having the above-described configuration will be described as below. The raw material mixed gas to be separated is supplied from a mixed gas source (not shown) to the first gas separation membrane unit 11 through a raw material mixed gas supply line 13. Prior to the supply, the raw material gas mixture is pressurized by the compression part 21, and the pressure thereof is increased. As the compression part 21, the same means as those used so far in the technical field can be used. For example, a compressor can be used.

The raw material gas mixture contains at least carbon dioxide and methane to be separated. When the mixed gas pressurized by the compression part 21 is supplied to the first gas separation membrane unit 11, the mixed gas is separated into a first permeated gas, which is a gas that has permeated the gas separation membrane, and a first non-permeated gas, which is a gas that has not permeated the gas separation membrane, due to a difference in permeation rate with respect to the gas separation membrane. In this system, carbon dioxide is a gas having a high permeation rate with respect to the gas separation membrane constituting each unit, that is, a high permeability gas, and methane is a gas having a low permeation rate with respect to the gas separation membrane constituting each unit, that is, a low permeability gas.

The non-permeated gas discharged from the first gas separation membrane unit 11 (Hereinafter, it is also referred to as ""first non-permeating gas"".) is a gas in which methane is concentrated as compared with a mixed gas as a raw material. The first non-permeated gas is discharged from the non-permeated gas outlet 11b of the first gas separation membrane unit 11, and is supplied to the second gas separation membrane unit 12 through the first non-permeated gas discharge line 14.

On the other hand, the first permeated gas discharged from the first gas separation membrane unit 11 is a gas in which carbon dioxide is concentrated as compared with a mixed gas as a raw material. A part of the first permeated gas is discharged from the first permeated gas outlet 11c of the first gas separation membrane unit 11, and is returned to the suction side of the compression part 21 in the raw material mixed gas supply line 13 via the first permeated gas recycle line 16. A part of the first permeated gas is taken out of the system through the first permeated gas discharge line 18.

The first non-permeated gas of the first gas separation membrane unit introduced into the second gas separation membrane unit 12 is separated into a second permeated gas and a second non-permeated gas by the unit 12. The second non-permeated gas discharged from the second gas separation membrane unit 12 is further enriched in methane, and is recovered from the second non-permeated gas outlet 12b of the unit 12 through the second non-permeated gas recovery line.

On the other hand, the second permeated gas is discharged from the second permeated gas outlet 12c of the second gas separation membrane unit 12, and is returned to the suction side of the compression part 21 in the raw material mixed gas supply line 13 via the second permeated gas recycle line 17 connected to the outlet 12c, port 12c.

The first permeated gas and the second permeated gas discharged from the first gas separation membrane unit 11 and the second gas separation membrane unit 12 and returned via the permeated gas recycle lines 16 and 17 are mixed with a mixed gas as a raw material, and then pressurized by the compression part 21.

The gas separation system of the present invention is characterized in that both the first permeated gas discharged from the first gas separation membrane unit and the second permeated gas discharged from the second gas separation membrane unit are mixed with a mixed gas as a raw material and supplied to the first gas separation membrane unit. With such a structure, the recovery rate of methane can be particularly improved.

The discharge flow rate F2 of the permeated gas discharged by the first permeated gas discharge line 18 in the permeated gas flow rate F1 in the first gas separation membrane unit 11 can be appropriately set based on the concentrations of methane and carbon dioxide in the raw material mixed gas and the raw material mixed gas flow rate. The larger the discharge flow rate F2 is, the more easily the recovery rate of methane is reduced. On the other hand, when the flow rate F2 is too small, the raw material supply compression power per unit time becomes too large, which is not desirable from the viewpoint of system operation efficiency and the viewpoint of increasing the required membrane area. From these viewpoints, subject matter as claimed, the ratio (F2/F1) of the flow rate F2 of the discharged permeated gas to the permeated gas flow rate F1 of the first gas separation membrane unit 11 is preferably 30% or more, and more preferably 40% or more. Further, the ratio (F2/F1) of the flow rate F2 of the discharged permeated gas to the permeated gas flow rate F1 of the first gas separation membrane unit 11 is preferably 99% or less from the viewpoint of improving the recovery rate of the gas B, and more preferably 98% or less. The unit of the flow rate is Nm³/h.

Subject matter as claimed, in order to efficiently obtain high-purity methane with a high recovery rate, the gas separation selectivity (permeation rate of carbon dioxide:

$P'_{CO2}$/methane: $P'_{CH4}$) of the gas separation membrane of the first gas separation membrane unit is preferably 5 or more and 100 or less, more preferably 10 or more and 90 or less, still more preferably 20 or more and 80 or less, and particularly preferably 30 or more and 80 or less. The gas separation selectivity (permeation rate of carbon dioxide: $P'_{CO2}$/methane: $P'_{CH4}$) of the gas separation membrane of the second gas separation membrane unit is preferably 5 or more and 100 or less, more preferably 10 or more and 90 or less, still more preferably 10 or more and 70 or less, and particularly preferably 10 or more and 60 or less.

Subject matter as claimed, in order to obtain high-purity methane with a high recovery rate while suppressing the compression power and the membrane area, the permeation rate $P'_{CO2}{}^1$ of carbon dioxide in the gas separation membrane of the first gas separation membrane unit is preferably $1.5 \times 10^{-5}$ cm³ (STP)/cm²·sec·cmHg or more and $100 \times 10^{-5}$ cm³ (STP)/cm²·sec·cmHg or less, more preferably $2 \times 10^{-5}$ cm³ (STP)/cm²·sec·cmHg or more and $80 \times 10^{-5}$ cm³ (STP)/cm²·sec·cmHg or less, still more preferably $3 \times 10^{-5}$ cm³ (STP)/cm²·sec·cmHg or more and $60 \times 10^{-5}$ cm³ (STP)/cm²·sec·cmHg or less, and particularly preferably $4 \times 10^{-5}$ cm³ (STP)/cm²·sec·cmHg or more and $40 \times 10^{-5}$ cm³ (STP)/cm²·sec·cmHg or less. The permeation rate of carbon dioxide of the gas separation membrane of the second gas separation membrane unit is preferably $1.5 \times 10^{-5}$ cm³ (STP)/cm²·sec·cmHg or more and $100 \times 10^{-5}$ cm³ (STP)/cm²·sec·cmHg or less, more preferably $2 \times 10^{-5}$ cm³ (STP)/cm²·sec·cmHg or more and $80 \times 10^{-5}$ cm³ (STP)/cm²·sec·cmHg or less, still more preferably $3 \times 10^{-5}$ cm³ (STP)/cm²·sec·cmHg or more and $70 \times 10^{-5}$ cm³ (STP)/cm²·sec·cmHg or less, and particularly preferably $4 \times 10^{-5}$ cm³ (STP)/cm²·sec·cmHg or more and $60 \times 10^{-5}$ cm³ (STP)/cm²·sec·cmHg or less.

Subject matter as claimed, in order to obtain high-purity methane with a high recovery rate while suppressing the compression power and the membrane area, the methane permeation rate $P'_{CH4}{}^1$ of the gas separation membrane of the first gas separation membrane unit and the methane permeation rate $P'_{CH4}{}^2$ of the gas separation membrane of the second gas separation membrane unit are preferably $0.03 \times 10^{-5}$ cm³ (STP)/cm²·sec·cmHg or more and $3 \times 10^{-5}$ cm³ (STP)/cm²·sec·cmHg or less, more preferably $0.05 \times 10^{-3}$ cm³ (STP)/cm²·sec·cmHg or more and $2.5 \times 10^{-5}$ cm³ (STP)/cm²·sec·cmHg or less, and most preferably $1.5 \times 10^{-5}$ cm³ (STP)/cm²·sec·cmHg or less.

The above gas separation selectivity and gas permeation rate preferably have the above selectivity and gas permeation rate at 40° C.

Subject matter as claimed, the reflux rate (That is, it is the ratio of the permeated gas flow rate F4 merged from the first gas separation membrane unit to the raw material mixed gas line through the first permeated gas recycle line to the gas flow rate F3 flowing into the first gas separation membrane unit (F4/F3).) from the first gas separation membrane unit is preferably 0.5% to 50%, for example, from the viewpoint of suppressing the membrane area and the compression power while maintaining high operation efficiency of the system and high purity of the product gas, and increasing the recovery rate of the gas B, and more preferably 1% to 40%. When the ratio (F4/F3) is low, the recovery rate becomes low, and when the ratio (F4/F3) is high, the required membrane area and the required compression power increase.

From the viewpoint of system operation efficiency and membrane area, the ratio (F4/(F0+F4)) of the permeated gas F4 to the total amount of the flow rate F0 of the raw material mixed gas flowing into the system and the permeated gas flow rate F4 of the first recycle line is preferably 50% or less, more preferably 30% or less, still more preferably 20% or less, still more preferably 15% or less, still more preferably 12% or less, and most preferably 10% or less. The lower limit of this ratio is preferably 0.1% or more, more preferably 0.5% or more, and particularly preferably 1% or more from the viewpoint of recovery rate and purity.

From the viewpoint of system operation efficiency and membrane area, the ratio (F2/(F0+F4)) of the permeated gas discharge flow rate F2 of the first permeated gas discharge line 18 to the total flow rate of the flow rate F0 of the raw material mixed gas and the permeated gas flow rate F4 of the first recycle line is preferably 50% or less, and more preferably 45% or less. The lower limit of this ratio is preferably 0.1% or more, more preferably 0.5% or more, and particularly preferably 1% or more from the viewpoint of recovery rate and purity.

Further, the reflux rate (That is, the ratio (F6/F5) of the flow rate F6 of the permeated gas that merges into the raw material mixed gas line from the second gas separation membrane unit 12 through the second permeated gas recycle line to the flow rate F5 of the gas that flows into the second gas separation membrane unit.) from the second gas separation membrane unit is, for example, preferably 60% or less from the viewpoint of suppressing the membrane area and the compression power while maintaining high operation efficiency of the system, and more preferably 50% or less. This ratio is usually 5% or more.

From the viewpoint of increasing the recovery rate, the ratio (F4/F1) of the recycle flow rate F4 by the first permeated gas recycle line to the permeated gas flow rate F1 in the first gas separation membrane unit 11 is preferably 0.5% or more, more preferably 5% or more, still more preferably 10% or more, and particularly preferably 20% or more.

From the viewpoint of reducing the membrane area, the ratio (F4/F1) of the recycle flow rate F4 by the first permeated gas recycle line to the permeated gas flow rate F1 in the first gas separation membrane unit 11 is preferably 60% or less, more preferably 40% or less, and still more preferably 30% or less. From the viewpoint of the balance between the recovery rate and the membrane area, the ratio (F4/F1) is preferably 0.5% or more and 60% or less, more preferably 5% or more and 40% or less, still more preferably 10% or more and 30% or less, and most preferably 20% or more and 30% or less."

Further, from the viewpoint of obtaining a balance between the purity and the recovery rate and the membrane area and the compression power, the reflux rate (That is, it is the ratio of the total flow rate of the permeated gas merged with the raw material mixed gas through each of the first permeated gas recycle line and the second permeated gas recycle line to the gas flow rate F3 flowing into the first gas separation membrane unit ((F4+F6)/F3).) in the gas separation system of the present invention is preferably, for example, 5% to 70% from the viewpoint of suppressing the membrane area and the compression power while maintaining high operation efficiency of the system and high purity of the product gas, and increasing the recovery rate of the gas B, and more preferably 10% to 60%.

The gas separation membrane in each of the gas separation membrane units 11 and 12 can be appropriately selected according to the type of the supplied mixed gas. As the gas separation membrane, the same membranes as those used in the art can be used without particular limitation. Examples thereof include rubber-like polymer materials such as silicone resins and polybutadiene resins, glass-like polymer materials such as polyimide, polyetherimide, polyamide, polyamideimide, polysulfone, polycarbonate, and cellulose, and ceramic materials such as zeolite. The gas separation membrane may be any of a homogeneous membrane, an asymmetric membrane composed of a homogeneous layer and a porous layer, and a microporous membrane. The gas separation membrane may be housed in the casing in any of a plate-and-frame type, a spiral type, and a hollow fiber type. A particularly suitable gas separation membrane is an aromatic polyimide hollow fiber gas separation membrane having a homogeneous layer thickness of 10 nm or more and 200 nm or less, a porous layer thickness of 20 μm or more and 200 μm or less, and an inner diameter of about 30 μm or more and 500 μm or less. In particular, subject matter as claimed, the gas separation membranes in the first gas separation membrane unit 11 and the second gas separation membrane unit 12 are preferably made of polyimide in view of durability, separation performance, and the like.

The raw material mixed gas used, subject matter as claimed, is a gas containing at least $CO_2$ and $CH_4$, and examples thereof include biogas, landfill gas, and natural gas. The biogas is a gas generated when a biomass raw material is brought into contact with a microorganism under anaerobic conditions to perform a fermentation process such as methane fermentation by the microorganism. Examples of the biomass raw material include organic matters such as food waste, agricultural residue, sewage sludge, and livestock waste. The landfill gas refers to a gas generated by microbial decomposition or the like of organic matter in a waste landfill. Biogas and landfill gas are typically composed primarily of $CO_2$ and $CH_4$. The composition of biogas or landfill gas may change during operation. In the gas separation system, since the type and the number of membrane modules in the system are normally set according to the composition of the raw material mixed gas, if the operation is continued as it is in a state where the ratio of $CH_4$ or $CO_2$ of the raw material mixed gas is increased or decreased during the operation, the purity of the product gas may be reduced or the recovery rate may be lowered. However, subject matter as claimed, by taking measures such as increasing or decreasing the ratio of F2/F1 with respect to the change in the composition, it is possible to prevent a decrease in purity and a decrease in recovery rate of the product gas during operation. Biogas and landfill gas may undergo such compositional changes during operation, but subject matter as claimed, high purity and high recovery rate of these gases can be maintained at low cost.

Subject matter as claimed, the raw material mixed gas preferably contains $CH_4$ in an amount of 30 mol % or more, particularly preferably 40 to 95 mol %. Further, subject matter as claimed, the raw material mixed gas preferably contains 3 to 70 mol % of $CO_2$, from the viewpoint of high technical significance of the gas separation system of the present invention, and particularly preferably contains 5 to 60 mol %.

The pressure of the compression part is generally preferably 0.2 MPaG or more and 3.0 MPaG or less, and more preferably 0.3 MPaG or more and 2.4 MPaG or less.

The operating temperature of each gas separation membrane unit is usually preferably 0° C. or higher and 80° C. or lower, and more preferably 5° C. or higher and 60° C. or lower.

Next, a gas separation system 10' according to a second embodiment of the present invention will be described with reference to FIG. 3. In the description of the second embodiment, components similar to those of the first embodiment are denoted by the same reference numerals, description thereof is omitted, and differences from the first embodiment will be mainly described.

Figure 3:
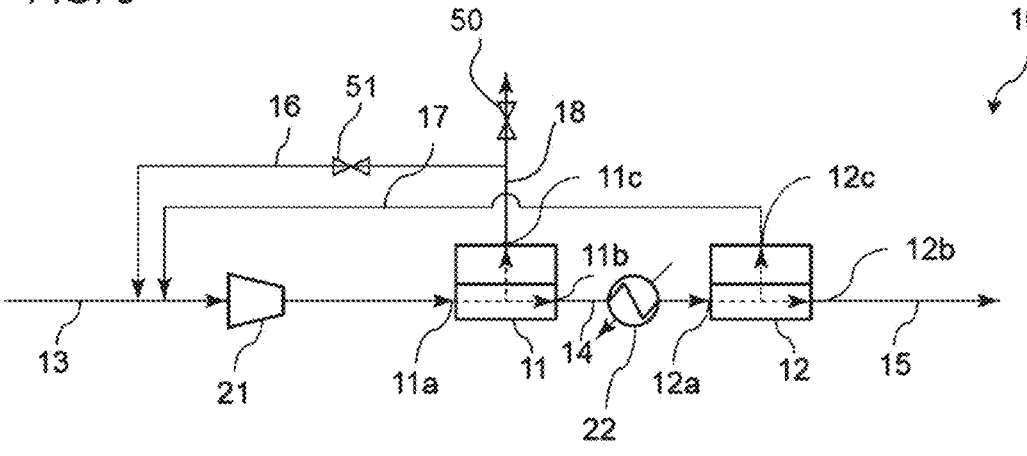
FIG. 3 is a schematic diagram showing a configuration of a gas separation system according to a second embodiment of the present invention.

In the gas separation system 10' shown in FIG. 3, the heating part 22 is disposed in the middle of the first non-permeated gas discharge line 14 connecting the non-permeated gas outlet 11b of the first gas separation membrane unit and the gas inlet 12a of the second separation membrane unit. The heating part 22 is installed for the purpose of heating the gas supplied to the second gas separation membrane unit 12 and setting the operation temperature of the unit 12 higher than the operation temperature of the first gas separation membrane unit 11. The heating part 22 includes, for example, a temperature sensor, a heater, and a control device that controls the temperature sensor and the heater. Subject matter as specified, the operation temperature of the gas separation membrane unit refers to the gas temperature at the inlet of the gas separation membrane unit while the mixed gas is supplied to the gas separation membrane unit (gas separation membrane module).

Subject matter as claimed, the operating temperature of the first gas separation membrane unit may be the same as or different from the operating temperature of the second gas separation membrane unit, but subject matter as embodied, the number of gas separation membrane modules used in the second gas separation membrane unit can be reduced by setting the operating temperature of the second gas separation membrane unit to be higher than the operating temperature of the first gas separation membrane unit.

In general, as the temperature of the gas separation membrane increases, the permeation rate of the gas passing through the gas separation membrane increases. Therefore, by setting the operation temperature of the second gas separation membrane unit to be higher than the operation temperature of the first gas separation membrane unit, it is possible to reduce the membrane area of the gas separation membrane module used in the second gas separation membrane unit while maintaining the purity and recovery rate of methane to be recovered. Subject matter as claimed, since the membrane area in the second gas separation membrane unit 12 for discharging the product gas tends to be large in order to increase the recovery rate or the like, the advantage of reducing the membrane area of the second gas separation membrane unit 12 is extremely remarkable.

Heating by the heating means 22 in the present embodiment is performed so that the operating temperature of the second gas separation membrane unit is higher than the operating temperature of the first gas separation membrane unit. The difference between the operating temperature of the second gas separation membrane unit and the operating temperature of the first gas separation membrane unit is preferably 5° C. or more and 40° C. or less, and more preferably 10° C. or more and 30° C. or less. The operating temperature of each gas separation membrane unit is preferably in the range of 0° C. or more and 80° C. or less as described above from the viewpoint of preventing condensation and suppressing heating energy, but may be 30° C. or more or 35° C. or more. In particular, when the operating temperature of the second gas separation membrane unit is higher than the operating temperature of the first gas separation membrane unit, the operating temperature of the first gas separation membrane unit is particularly preferably 5 to 60° C., and even more preferably 10 to 50° C. The operating temperature of the second gas separation membrane unit is particularly preferably 15 to 80° C., and even more preferably 20 to 70° C.

A gas separation system according to a third embodiment of the present invention will be described.

Subject matter as claimed, the gas separation selectivity of the first gas separation membrane unit may be the same as or different from the gas separation selectivity of the second gas separation membrane unit, but by making the gas separation selectivity of the second gas separation membrane unit lower than the gas separation selectivity of the first gas separation membrane unit, the number of gas separation membrane modules used in the second gas separation membrane unit can be reduced."

As described above, the gas separation membrane has a lower gas permeation rate as the gas separation selectivity is higher, and the gas separation membrane has a lower gas separation selectivity as the gas permeation rate is higher. Therefore, by making the gas separation membrane constituting the first gas separation membrane unit and the separation membrane constituting the second gas separation membrane unit be gas separation membranes having different gas separation selectivity and making the gas separation selectivity of the gas separation membrane of the second gas separation membrane unit lower than the gas separation selectivity of the gas separation membrane of the first gas separation membrane unit, it is possible to reduce the membrane area (number) of the gas separation membrane modules used in the second gas separation membrane unit while maintaining the purity and recovery rate of methane to be recovered.

Subject matter as embodied, when the gas separation selectivity at 40° C. of the gas separation membrane of the first gas separation membrane unit is 1.0, the gas separation selectivity of the gas separation membrane of the second gas separation membrane unit is preferably less than 1.0, more preferably 0.1 or more and 0.9 or less, and particularly preferably 0.2 or more and 0.8 or less. Here, the gas separation selectivity is a separation selectivity of carbon dioxide ($CO_2$) and methane ($CH_4$), and is represented by a ratio of (permeation rate of carbon dioxide: $P'_{CO2}$/permeation rate of methane: $P'_{CH4}$).

Subject matter as embodied, when the permeation rate $P'_{CO2}{}^1$ of carbon dioxide in the gas separation membrane of the first gas separation membrane unit at 40° C. is 1.0, the permeation rate $P'_{CO2}{}^2$ of carbon dioxide in the gas separation membrane of the second gas separation membrane unit is preferably greater than 1.0, more preferably greater than or equal to 1.2 and less than or equal to 8, and particularly preferably greater than or equal to 1.5 and less than or equal to 7.

Subject matter as embodied, when the methane permeation rate $P'_{CH4}{}^1$ of the gas separation membrane of the first gas separation membrane unit at 40° C. is 1.0, the methane permeation rate $P'_{CH4}{}^2$ of the gas separation membrane of the second gas separation membrane unit is preferably more than 1.0, more preferably 1.5 or more and 30 or less, and particularly preferably 2 or more and 20 or less.

Subject matter as claimed, the second embodiment and the third embodiment may be combined. That is, by setting the operation temperature of the second gas separation membrane unit to be higher than the operation temperature of the first gas separation membrane unit and setting the gas separation selectivity of the first gas separation membrane unit to be higher than the gas separation selectivity of the second gas separation membrane unit, it is possible to further reduce the number of gas separation membrane modules used in the second gas separation membrane unit while maintaining the purity and recovery rate of methane to be recovered.

When the methane gas separated and recovered using the gas separation system of the present embodiment is supplied to a municipal gas line or the like, a gas compressor as a compression unit may be provided in the middle of the second non-permeated gas recovery line 15 to increase the pressure of the methane gas.

Although subject matter as claimed has been described based on the preferred embodiments thereof, subject matter as claimed is not limited to the embodiments. For example, in the above embodiment, as an example of each gas separation membrane unit, a unit constituted by a gas separation membrane module having a hollow fiber membrane is used.

Further, in addition to the compression part in the above-described embodiment, a decompression part may be provided on any one or two permeation sides of each gas separation membrane unit to apply power to the mixed gas supplied to each gas separation membrane unit to pass through the separation membrane. As such a pressure reducing device, a known vacuum pump or the like can be used.

EXAMPLES

Hereinafter, subject matter as claimed will be described in more detail with reference to Examples. However, the scope of subject matter as claimed is not limited by these examples.

<Gas Separation Membrane Module>

The gas separation characteristics at 40° C. of the gas separation membrane modules used in Examples are shown in Table 1. In this gas separation membrane module, a gas separation membrane composed of a polyimide hollow fiber membrane is housed in a case. The gas separation membrane module A is composed of a gas separation membrane having higher gas separation selectivity and lower gas permeation rate than the gas separation membrane module B.

The units $P'_{CO2}$ and $P'_{CH4}$ in Table 1 are ×10.5 cm³ (STP)/cm²·sec·cmHg."

TABLE 1

| Separation membrane module | $P'_{CO2}$ | $P'_{CH4}$ | $P'_{CO2}/P'_{CH4}$ | Membrane area per one module m² |
|---|---|---|---|---|
| A | 9.9 | 0.18 | 55 | 24 |
| B | 21 | 0.82 | 26 | 20 |

Example 1

A mixed gas containing carbon dioxide and methane was separated using the gas separation system 10 shown in FIG. 1 to obtain methane as a product gas. Each of the first gas separation membrane unit 11 and the second gas separation membrane unit 12 is composed of a gas separation membrane module A. A compressor was used as the compression part 21 in the system 10. The raw material gas mixture has a temperature of 35° C., is heated by compression by a compression part, is cooled by a cooling device (not shown), and is supplied to each gas separation membrane unit. The flow rate (flow rate flowing into the system) and composition of the raw material mixed gas, the flow rate flowing into each unit and the flow rate discharged from each outlet, and the flow rate (F4) of the first permeated gas recycle line were as shown in Table 2 below."

Example 2

A product gas was obtained in the same manner as in Example 1 except that the operating temperature of the second gas separation membrane unit 12 was changed as shown in Table 2 below. The gas separation selectivity of the second gas separation membrane unit 12 at 50° C. is 0.86 times the gas separation selectivity of the second gas separation membrane unit 12 at 40° C.

Example 3

A product gas was obtained in the same manner as in Example 1 except that the second gas separation membrane unit 12 was constituted by the gas separation membrane module B.

Example 4

A product gas was obtained in the same manner as in Example 1 except that the second gas separation membrane unit 12 was composed of the gas separation membrane module B and the operating temperature was changed as shown in Table 2 below.

Comparative Example 1 to Comparative Example 4

In the system of FIG. 1, a system of a comparative example similar to that of FIG. 1 was used except that the first permeated gas recycle line 16 was not provided and the entire amount of the first permeated gas was discharged to the outside of the system. The system of this comparative example corresponds to PTL 2. Product gases were obtained in the same manner as in Examples 1 to 4 except for this point.

Example 5 to Example 8

The flow rate (F4) of the first permeated gas recycle line was set to the value shown in Table 2. Except for this point, a product gas was obtained in the same manner as in Example 1.

Example 9 to Example 12

The second gas separation membrane unit 12 was composed of the gas separation membrane module B, and the flow rate (F4) of the first permeated gas recycle line was set to a value shown in Table 2. Except for this point, a product gas was obtained in the same manner as in Example 1.

TABLE 2

| | Raw material mixed gas | | | | Operating temperature | | Gas separation selectivity[1]) | |
| | Flow rate | Composition | | Operating | First gas separation membrane | Second gas separation membrane | First gas separation | Second gas separation |
| | (FO) Nm³/h | CO$_2$ mol % | CH$_4$ mol % | pressure MPaG | unit °C. | unit °C. | membrane unit | membrane unit |
|---|---|---|---|---|---|---|---|---|
| Example 1 | 1000 | 40 | 60 | 1.0 | 40 | 40 | 1.00 | 1.00 |
| Example 2 | 1000 | 40 | 60 | 1.0 | 40 | 50 | 1.00 | 1.00 |
| Example 3 | 1000 | 40 | 60 | 1.0 | 40 | 40 | 1.00 | 0.46 |
| Example 4 | 1000 | 40 | 60 | 1.0 | 40 | 50 | 1.00 | 0.46 |
| Comp. Example 1 | 1000 | 40 | 60 | 1.0 | 40 | 40 | 1.00 | 1.00 |
| Comp. Example 2 | 1000 | 40 | 60 | 1.0 | 40 | 50 | 1.00 | 1.00 |
| Comp. Example 3 | 1000 | 40 | 60 | 1.0 | 40 | 40 | 1.00 | 0.46 |
| Comp. Example 4 | 1000 | 40 | 60 | 1.0 | 40 | 50 | 1.00 | 0.46 |
| Example 5 | 1000 | 40 | 60 | 1.0 | 40 | 40 | 1.00 | 1.00 |
| Example 6 | 1000 | 40 | 60 | 1.0 | 40 | 40 | 1.00 | 1.00 |
| Example 7 | 1000 | 40 | 60 | 1.0 | 40 | 40 | 1.00 | 1.00 |
| Example 8 | 1000 | 40 | 60 | 1.0 | 40 | 40 | 1.00 | 1.00 |
| Example 9 | 1000 | 40 | 60 | 1.0 | 40 | 40 | 1.00 | 0.46 |
| Example 10 | 1000 | 40 | 60 | 1.0 | 40 | 40 | 1.00 | 0.46 |
| Example 11 | 1000 | 40 | 60 | 1.0 | 40 | 40 | 1.00 | 0.46 |
| Example 12 | 1000 | 40 | 60 | 1.0 | 40 | 40 | 1.00 | 0.46 |

| | Flow rate | | | | | | | |
| | First gas separation membrane unit (F3) Nm³/h | First permeated gas (F1) Nm³/h | Discharge permeated gas (F2) Nm³/h | First permeated gas recycle line (F4) Nm³/h | F2/F1 (%) | F4/F1 (%) | Second gas separation membrane unit (F5) Nm³/h | Second permeated gas recycle line (F6) Nm³/h |
|---|---|---|---|---|---|---|---|---|
| Example 1 | 1233 | 436 | 406 | 30 | 93 | 7 | 797 | 203 |
| Example 2 | 1246 | 436 | 406 | 30 | 93 | 7 | 810 | 216 |
| Example 3 | 1299 | 436 | 406 | 30 | 93 | 7 | 863 | 269 |
| Example 4 | 1322 | 437 | 407 | 30 | 93 | 7 | 886 | 292 |
| Comp. Example 1 | 1193 | 409 | 409 | 0 | 100 | 0 | 784 | 193 |
| Comp. Example 2 | 1205 | 409 | 409 | 0 | 100 | 0 | 796 | 205 |
| Comp. Example 3 | 1254 | 409 | 409 | 0 | 100 | 0 | 845 | 254 |
| Comp. Example 4 | 1275 | 409 | 409 | 0 | 100 | 0 | 866 | 275 |
| Example 5 | 1263 | 454 | 404 | 50 | 89 | 11 | 809 | 213 |
| Example 6 | 1337 | 500 | 400 | 100 | 80 | 20 | 836 | 237 |
| Example 7 | 1574 | 642 | 392 | 250 | 61 | 39 | 932 | 324 |
| Example 8 | 1853 | 786 | 386 | 400 | 49 | 51 | 1066 | 453 |
| Example 9 | 1332 | 454 | 404 | 50 | 89 | 11 | 878 | 282 |
| Example 10 | 1413 | 501 | 401 | 100 | 80 | 20 | 912 | 313 |
| Example 11 | 1676 | 642 | 392 | 250 | 61 | 39 | 1034 | 426 |
| Example 12 | 1991 | 786 | 386 | 400 | 49 | 51 | 1204 | 591 |

| | Number of modules | | | Product gas | |
| | First gas separation membrane unit pc | Second gas separation membrane unit pc | Sum pc | Purity of CH$_4$ mol % | Recovery rate of CH$_4$ % |
|---|---|---|---|---|---|
| Example 1 | 31 | 74 | 105 | ≥97.0 | 96.0 |
| Example 2 | 31 | 64 | 95 | ≥97.0 | 96.0 |
| Example 3 | 31 | 32 | 63 | ≥97.0 | 96.0 |
| Example 4 | 31 | 30 | 61 | ≥97.0 | 96.0 |
| Comp. Example 1 | 31 | 73 | 104 | ≥97.0 | 95.6 |
| Comp. Example 2 | 31 | 63 | 94 | ≥97.0 | 95.6 |
| Comp. Example 3 | 31 | 31 | 62 | ≥97.0 | 95.6 |
| Comp. Example 4 | 31 | 29 | 60 | ≥97.0 | 95.6 |
| Example 5 | 31 | 76 | 107 | ≥97.0 | 96.4 |
| Example 6 | 31 | 80 | 111 | ≥97.0 | 97.0 |
| Example 7 | 31 | 91 | 122 | ≥97.0 | 98.3 |
| Example 8 | 31 | 103 | 134 | ≥97.0 | 99.3 |
| Example 9 | 31 | 33 | 64 | ≥97.0 | 96.4 |
| Example 10 | 31 | 35 | 66 | ≥97.0 | 97.0 |
| Example 11 | 31 | 41 | 72 | ≥97.0 | 98.4 |
| Example 12 | 31 | 48 | 79 | ≥97.0 | 99.3 |

[1]Relative value with respect 1.00 which is gas separation membrane of first gas separation membrane unit From the comparison of the results of Examples 1 to 4 and Comparative Examples 1 to 4 in Table 2, it can be seen that the gas separation system of the present invention can obtain high purity methane at a higher recovery rate from the raw material mixed gas containing carbon dioxide and methane while keeping the necessary increase in the membrane area and compression power to a certain level or less, as compared with each Comparative Example in which the permeated gas is not refluxed from the first gas separation membrane unit.

Further, from the comparison between Examples 1 and 3 and Examples 2 and 4, it was found that the number of gas separation membrane modules used in the second gas separation membrane unit can be reduced while maintaining the purity and recovery rate of methane to be recovered by setting the operation temperature of the second gas separation membrane unit to be higher than the operation temperature of the first gas separation membrane unit. Further, from the comparison between Examples 1 and 2 and Examples 3 and 4, it was found that the number of gas separation membrane modules used in the second gas separation membrane unit can be reduced while maintaining the purity and recovery rate of methane to be recovered by making the gas separation selectivity of the gas separation membrane of the second gas separation membrane unit lower than the gas separation selectivity of the gas separation membrane of the first gas separation membrane unit.

Further, from the comparison between Example 1 and Examples 5 to 8 and the comparison between Example 3 and Examples 9 to 12, it is found that, subject matter as claimed, by adjusting the ratio of the recycle amount F4 by the first permeated gas recycle line to the permeated gas flow rate F1 of the first gas separation membrane unit to a predetermined range, it is possible to effectively improve the recovery rate while keeping the degree of increase in the membrane area to a certain degree or less."

INDUSTRIAL APPLICABILITY

According to the present invention, high-purity methane can be obtained at a high recovery rate from a raw material mixed gas containing at least carbon dioxide and methane.

The invention claimed is:

1. A gas separation system for enriching methane contained in raw material mixed gas comprising at least carbon dioxide and methane by supplying the raw material mixed gas to gas separation membrane unit, wherein:

the gas separation system comprises a first gas separation membrane unit and a second gas separation membrane unit;

each of the gas separation membrane units comprise at least a gas inlet, a permeated gas outlet, and a non-permeated gas outlet;

the raw material mixed gas contains 30 mol % or more of $CH_4$ and 3 to 70 mol % of $CO_2$, the non-permeated gas outlet of the first gas separation membrane unit and the gas inlet of the second gas separation membrane unit are connected by a non-permeated gas discharge line;

the raw material mixed gas supply line is connected to the gas inlet of the first gas separation membrane unit, a compressor is interposed in the raw material mixed gas supply line, and a first permeated gas recycle line connects the permeated gas outlet of the first gas separation membrane unit and a position on a suction side of the compressor on the raw material mixed gas supply line;

the first permeated gas recycle line comprises a permeated gas discharge line for at least partially discharging the permeated gas discharged from the first gas separation membrane unit to the outside of the gas separation system, and no gas separation membrane is interposed in the first permeated gas recycle line;

the permeated gas outlet of the second gas separation membrane unit and a position on the suction side of the compressor in the raw material mixed gas supply line are connected by a second permeated gas recycle line;

enriched methane is recovered from the non-permeated gas outlet of the second gas separation membrane unit, and a ratio of a recycle flow rate F4 circulated to the first gas separation membrane unit by the first permeated gas recycle line to a permeated gas flow rate F1 of the first gas separation membrane unit is 0.5% or more and 60% or less.

2. The gas separation system of claim 1, wherein the operating temperature of the first gas separation membrane unit is different from that of the second gas separation membrane unit.

3. The gas separation system of claim 2, wherein the operating temperature of the second gas separation membrane unit is higher than that of the first gas separation membrane unit.

4. The gas separation system of claim 3, wherein a heater is disposed in the middle of the non-permeated gas discharge line connecting the non-permeated gas outlet of the first gas separation membrane unit and the gas inlet of the second gas separation membrane unit.

5. The gas separation system of claim 1, wherein the gas separation selectivity of the first gas separation membrane unit is different from that of the second gas separation membrane unit.

6. The gas separation system of claim 5, wherein gas separation selectivity of the second gas separation membrane unit is lower than that of the first gas separation membrane unit.

7. The gas separation system of claim 1, wherein the raw material mixed gas contains 40 to 95 mol % of $CH_4$ and 5 to 60 mol % of $CO_2$.

8. The gas separation system of claim 1, wherein a pressure of the compressor is 0.2 MPaG or more and 3.0 MPaG or less.

9. The gas separation system of claim 1, wherein a ratio of a flow rate F2 of the permeated gas discharged through the first permeated gas discharge line to the permeated gas flow rate F1 of the first gas separation membrane unit is 30% or more and 99% or less.

10. The gas separation system of claim 3, wherein a difference between the operating temperature of the second gas separation membrane unit and the operating temperature of the first gas separation membrane unit is 5° C. or more and 40° C. or less.

11. The gas separation system of claim 1, wherein gas separation membranes in the first and second gas separation membrane units are hollow fiber gas separation membranes made of an aromatic polyimide having an asymmetric structure in which a thickness of a homogeneous layer is 10 nm or more and 200 nm or less, and a thickness of a porous layer is 20 μm or more and 200 μm or less.

12. The gas separation system of claim 6, wherein when a gas separation selectivity ($CO_2/CH_4$) of the gas separation membrane of the first unit at 40° C. is normalized to 1.0, a gas separation selectivity of the gas separation membrane in the second gas separation membrane unit is 0.1 or more and 0.9 or less.

13. The gas separation system of claim 1, wherein a methane permeation rate $P'_{CH4}{}^1$ of the gas separation membrane in the first gas separation membrane unit and a methane permeation rate $P'_{CH4}{}^2$ of the gas separation membrane in the second gas separation membrane unit are each $0.03 \times 10^{-5}$ cm3 (STP)/cm2·sec·cmHg or more and $3 \times 10^{-5}$ cm3 (STP)/cm2·sec·cmHg or less at 40° C.

\*   \*   \*   \*   \*